US009668755B2

(12) United States Patent
Biegun

(10) Patent No.: US 9,668,755 B2
(45) Date of Patent: Jun. 6, 2017

(54) SURGICAL INSTRUMENT FOR THE REMOVAL OF BONE WITH SHARP TEETH AND THE METHOD OF FORMATION THEREOF

(71) Applicant: Jean-Francois Biegun, Bavilliers (FR)

(72) Inventor: Jean-Francois Biegun, Bavilliers (FR)

( * ) Notice: Subject to any disclaimer, the term of this patent is extended or adjusted under 35 U.S.C. 154(b) by 339 days.

(21) Appl. No.: 13/755,074

(22) Filed: Jan. 31, 2013

(65) Prior Publication Data

US 2013/0200550 A1     Aug. 8, 2013

(30) Foreign Application Priority Data

Feb. 2, 2012  (FR) ..................... 12 00310

(51) Int. Cl.
*A61B 17/16* (2006.01)
*B29C 45/14* (2006.01)
*A61B 17/00* (2006.01)

(52) U.S. Cl.
CPC ...... *A61B 17/1659* (2013.01); *A61B 17/1668* (2013.01); *B29C 45/14631* (2013.01); *A61B 2017/00526* (2013.01)

(58) Field of Classification Search
CPC ... B29C 70/78; B29C 43/18; B29C 45/14467; B29C 45/14631; B29C 70/68; B29C 70/70; B29C 70/72; B29C 2043/181; B29C 2043/182; B29C 45/1463; B29C 45/14008; B29C 45/14819; A61B 17/1668; A61B 2017/00526; A61B 17/1659

USPC ......... 264/279.1, 279, 275, 271.1, 259, 510, 264/516, DIG. 64, 328.7; 606/82, 85
See application file for complete search history.

(56) References Cited

U.S. PATENT DOCUMENTS

| | | | | |
|---|---|---|---|---|
| 5,124,106 A | * | 6/1992 | Morr et al. | 264/221 |
| 5,665,091 A | * | 9/1997 | Noble | A61B 17/1659 606/79 |
| 2006/0111725 A1 | * | 5/2006 | Biegun | 606/85 |
| 2011/0196374 A1 | | 8/2011 | Porte et al. | |
| 2011/0278769 A1 | * | 11/2011 | Ehbing | B29C 33/0061 264/446 |

FOREIGN PATENT DOCUMENTS

| | | | | |
|---|---|---|---|---|
| EP | 2 147 642 A2 | | 1/2010 | |
| FR | 2903591 A1 | * | 1/2008 | A61L 31/129 |

OTHER PUBLICATIONS

FR 2903591 A1. Machine Translation.*
French Search Report (FR 1200310) (2 pages—dated May 2, 2012).

* cited by examiner

*Primary Examiner* — Matthew Daniels
*Assistant Examiner* — Leith S Shafi
(74) *Attorney, Agent, or Firm* — Renner, Kenner, Greive, Bobak, Taylor & Weber

(57) ABSTRACT

Surgical instrument for the removal of bone material with a surface from which at least one tooth projects, preferably teeth made from plastic material designed to come into contact with bone to remove a portion thereof, characterized in that the width (1) of the tooth or each tooth (5), that is the smallest width dimension at the level of the said one surface of the instrument from which it projects, is between 1 mm and 7 mm, preferably between 2 mm and 5 mm, more preferably between 3 mm and 4 mm.

10 Claims, 1 Drawing Sheet

SURGICAL INSTRUMENT FOR THE REMOVAL OF BONE WITH SHARP TEETH AND THE METHOD OF FORMATION THEREOF

TECHNICAL FIELD

The present invention relates to a method for producing a surgical instrument, in particular of the type that has an area intended for acting on a bone for removing apart thereof, for example cutting it or rasping it, for example a femoral rasp, a cotyl cutter, a hip rasp of the like. The present invention also relates to a method for producing a surgical device designed to withstand increased stress during its use, either when it acts on the bone as above or when it supports a surgical instrument which performs the action on the bone, for example a device for guiding the cutting. The present invention also relates to a surgical instrument and a surgical device which can be obtained by a method of production of this kind.

BACKGROUND ART

From the prior art, and in particular from the international application WO 2004/047655 in the name of the Applicant, surgical instruments or devices of this kind are already known, where the parts designed to be subjected to heavy stress when acting on the bone for removing a part thereof are made of plastic material. These parts can in particular comprise teeth made of plastic and can be produced by moulding.

This makes it possible to produce them on a large scale at low cost and thus encourages single use, which prevents re-sterilisation, previously prohibited.

From U.S. Pat. No. 5,665,091 a hip rasp is known, the teeth of which can be made from a polymer material.

However, the production of these rasps is performed solely by machining. If this rasp were made by moulding, not described in this document of the prior art, it would not be possible to obtain sufficiently sharp teeth, only machining (preferably using metal material) makes it possible to obtain the sharp teeth described in this document of the prior art. In fact, although these surgical instruments and devices of the prior art are clearly more advantageous than what was previously available, in particular in that, although made from a plastic material they make it possible to rasp or cut the bone and/or withstand the stresses associated with such actions, it would be desirable to improve further their ability to cut and/or withstand stress and at the same time produce them using a simple moulding method that is suitable for mass production.

DISCLOSURE OF THE INVENTION

The present invention thus provides a method for producing a surgical instrument or device for acting on bone and removing a part of the latter, one part of which intended to withstand the increased stress associated with this action is made of plastic material, said plastic part being able to comprise at least one tooth, preferably a plurality of teeth projecting from the exterior of the instrument, and designed to act on the bone directly.

Preferably, the dimensions of the first part are greater than the dimensions of the plastic part intended to withstand increased stress, in particular are significantly greater.

By providing the moulding of the plastic part withstanding increased stress on the basis of a moulding of a small dimension relative to the total dimension of the instrument, it is ensured that the plastic part can withstand increased pressures more effectively, in particular in its capacity of acting on the bone. Thus, for example in the case of a plastic part comprising cutting or rasping teeth, the inventors have understood for the first time that the rasping ability of the rasps of the prior art was limited by the fact that it was not possible to form teeth by moulding a narrow width and/or a large height and therefore a sharp profile, as the plastic material flowed into the mould did not manage to penetrate as far as the bottom of the mould cavities provided for forming the teeth. Thus in the prior art the teeth, once removed from their mould, did not have the right profile to be sufficiently effective. According to the invention for the first time a surgical instruments obtained by moulding has been obtained with teeth made of plastic materials which are particularly suitable for acting on bone.

According to one embodiment of the invention the preform is placed in the mould to form the final instrument and plastic material is flowed into the remaining space, including the space of the teeth, if provided; the dimensions of the mould relative to those of the prefrom being selected so that this space remains small, the final product obtained then having an interface between the preform and the part designed to withstand increase stress, in particular the part comprising teeth, if there are any.

According to another embodiment teeth are provided and means are provided in the mould of the instrument for stopping the openings of the mould cavities of the teeth and then the mould is completely filled with moulding material with the exception of the teeth cavities, the stopping means are removed to allow the moulding material to pass into the cavities.

According to this embodiment there is then no interface between the plastic materials of the preform and the part designed to withstand stress, in particular the part with teeth. In particular, the stopping means can comprise spring means which are pushed away by the pressure of the moulding material which accumulates in the mould so as to free the moulding cavities of the teeth, accumulated pressure which after the release of the mould cavities effectively pushes the plastic moulding material into the teeth cavities, so as to obtain in this way teeth corresponding exactly to the form of the cavities.

According to a preferred embodiment of the invention, the preform is obtained by a previous overmoulding stage around a metal insert, in particular a metal rod, an intermediate body made of plastic material to obtain in this way the preform made from the metal part surrounded by the plastic material.

According to another advantageous embodiment the preform is made entirely from a metal material.

The present invention also relates to a surgical instrument for removing bone material.

Preferably, the height of the tooth or each tooth, i.e. the distance between its tip and the said one surface is greater than or equal to 1 mm, in particular is between 1 mm and 8 mm.

Preferably, the ratio of the height to the width is greater than 0.2, in particular is between 0.3 and 2.

Preferably, the at least one tooth has in transverse cross section a pointed or sharp-edged tip.

Preferably, the angle formed by the tooth at the tip is between 0° and 120°, in particular between 60° and 110°.

The present invention also relates to a surgical device or instrument comprising an interior part and an exterior part designed to withstand increased stress during the removal of material by means of the instrument or the device, said exterior part being made of plastic material and being able in particular to comprise one tooth or teeth and the exterior part intended to withstand stress being overmoulded onto the interior part, in particular by surrounding it, by forming an interface between the material of the interior part and the plastic material of the exterior part.

Preferably, the interior part is at least partly made of plastic material and this at least one part is separated from the exterior part made of plastic material by said one interface.

According to a preferred embodiment of the invention the plastic material for forming the at least one part of the interior part is identical to the plastic material used for the exterior part.

According to a preferred embodiment of the invention the interior part is formed by a part made of metal material, for example a metal bar, around which a plastic material is overmoulded, thus making a preform forming the interior part of the surgical instrument, the exterior part made of plastic material being overmoulded onto or around the preform.

Preferably, two blind holes hollowed into the exterior part made of plastic material lead to the exterior of the instrument, the bottoms of the blind holes being formed respectively by the plastic material of the preform.

These two blind holes correspond to the two pins which hold the preform in the mould during the moulding of the exterior part made of plastic material.

BRIEF DESCRIPTION OF THE DRAWINGS

By way of example a preferred embodiment of the invention is now be described with reference to the drawing in which.

PREFERRED EMBODIMENT FOR CARRYING OUT THE INVENTION

FIGS. 1 to 4 show different stages for obtaining a rasp according to the invention.

Figure 1:
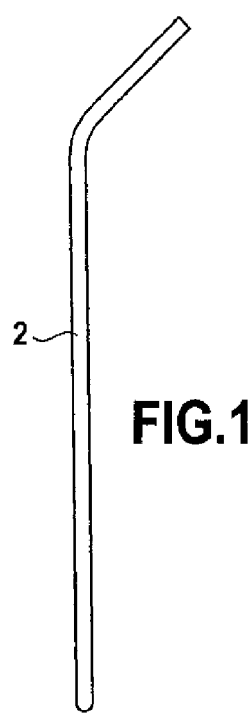
FIG. 1 shows a metal rod designed to form part of a hip rasp according to the invention.
Figure 2:
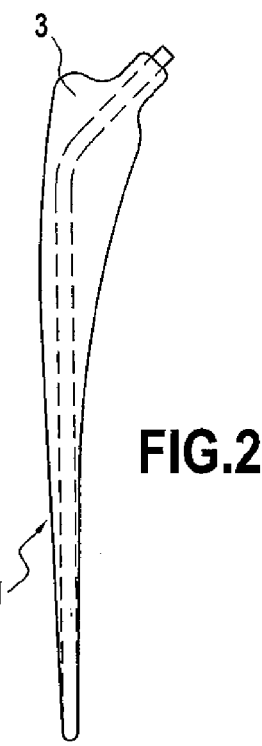
FIG. 2 shows the preform obtained after overmoulding around the metal part of FIG. 1 with a plastic material.
Figure 3:
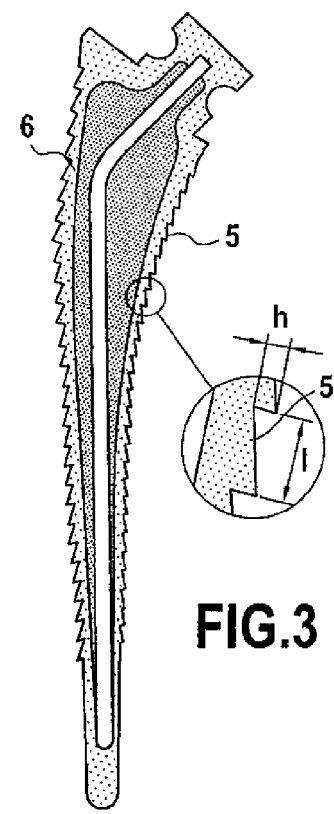
FIG. 3 shows a cross section of the anterior-posterior plane of the final rasp after overmoulding around the preform of FIG. 2 of the part intended to act on the bone.
Figure 4:
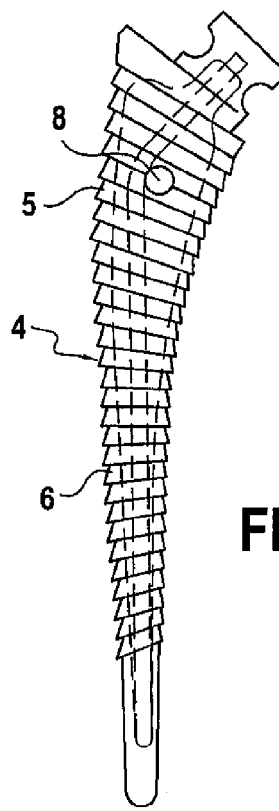
FIG. 4 is a side view of the final rasp.
Figure 5:
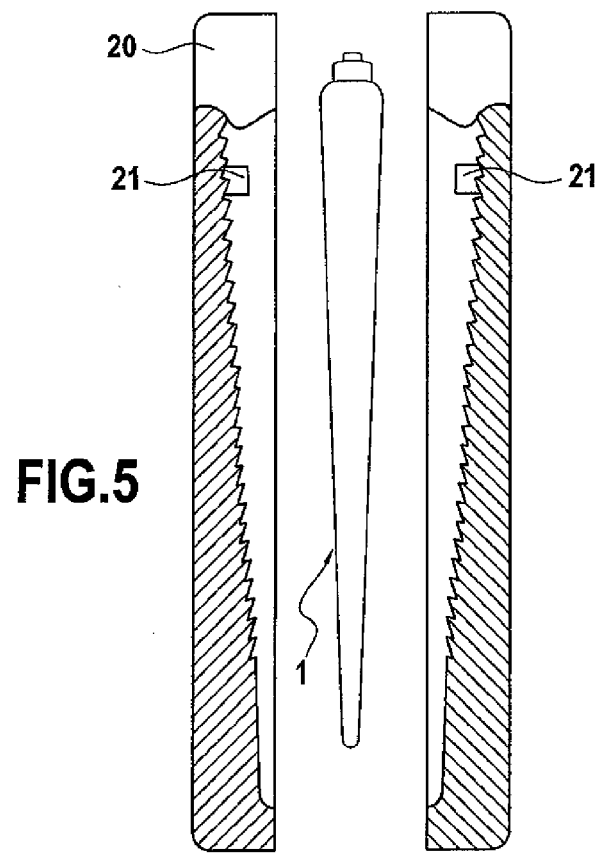
FIG. 5 is a side view of the mould used to form the rasp of FIGS. 3 and 4.

FIG. 4 shows a rasp 4 according to the invention. It comprises an interior or central part 1 formed by a rod 2 made of metal material around which a part 3 made of plastic material has been moulded. The part 3 made of plastic material and the rod 2 joined together in this way form a preform.

This preform was obtained by moulding, in particular by injection moulding, around the metal part which was held in the first mould by two first lateral pins. As a result in said preform 1 two holes are formed leading to the outside of the preform and going up to the rod 2. These two holes correspond to the form of the two first pins which hold the rod 2 in the first mould.

Then, the preform or interior or central part 1 formed by the rod 2 and the section 3 moulded around it, is itself positioned in a second mould 20 which on its internal walls has small cavities designed to form complementary teeth or teething 5 intended to act on the bone during the use of the rasp.

Once the central section 1 is arranged in the second mould and also held by two second pins 21 on either side, the plastic material is poured in the form of a layer 6 which surrounds it completely and fills the cavities for forming the teeth. At the exit of the mould, once the plastic moulding material forming the layer 6 comprising the teeth has hardened, the final rasp 4 is obtained. On its sides it has two blind holes 8 traversing the layer 6 corresponding to the second holding pins 21. The holes 8 leading to the exterior and their bottom is formed by the material of the central part 3.

These blind holes corresponding to the second holding pins for the central part in the second mould during the overmoulding of the layer 6 no longer have the metal part 2 as a base, like those of the preform, but have the plastic part of the preform 1 as a base. Thus, the advantage is that during the washing of the rasp, in particular with a liquid, in particular water, the latter can no longer come into direct contact with the metal part 2 on the inside of the rasp, which prevents the occurrence of corrosion that would harm the biocompatibility of the rasp.

According to the invention it is possible to make the part 3 completely from plastic material, i.e. without having the metal reinforcing part 2. Likewise instead of having only one plastic material or surrounding a metal part to make the part 3 it is possible to provide a single metal element.

If the part 3 is made from plastic material, said plastic material may be identical to the plastic material used for the layer 6 forming the teeth 5, or may be different according to the requirements.

For the plastic materials it is possible to use polyoxymethylenes, polyamides, polyethylenes, liquid crystalline polymers, polyvinyl fluorides, PMMA, but also semi-aromatic, semi-crystalline polyaryl amides.

Preferably, if the plastic material selected is not sufficiently hard to rasp the bone it is preferable to treat it with β or γ rays to increase its hardness and enable it to be used as a rasp for rasping bone. Preferably, the γ radiation is performed by exposure to a dose of 25 to 50 kGray. If the appropriate doses are maintained the effect of the γ radiation is on the one hand to sterilise the part thus avoiding the necessity of re-sterilising it and on the other hand to harden the plastic material to enable it to rasp the bone. Furthermore, once this first sterilisation by γ rays has been used it is no longer possible to re-sterilise the rasp, in particular by placing it in an autoclave, which thus avoids an improper reuse of the rasp. The surgeon no longer has any choice but to discard it after use.

According to the invention the teeth are perfectly formed. In fact it has been taken into account for the first time that when a rasp of this kind made from plastic material was wanted, the problem was that the teeth were not very sharp. This was due, and the inventors have taken this into account, to the fact that the sizes of the moulding cavities for the teeth were small and when a large amount of plastic material is poured in these cavities have a tendency not to fill up, as they are too small and there is a vacuum effect in the mould cavity. As a result in the prior art teeth were not moulded correctly which made it impossible to use the rasp. According to the invention however very "sharp" teeth are obtained. In fact, the pressure on the plastic material forming the skin layer 6 is stronger to push the plastic material into the moulding cavities of the teeth 5, as the total volume of the layer 6 is much smaller than the total volume of the rasp, which was not the case in the moulding systems of the prior art.

The principle of producing a rasp according to the invention has been described. Of course, the same principle can be applied to other cutting devices intended for acting on bone and comprising teeth or having parts intended to withstand heavy stress associated with the cutting of the bone. Thus the same principle can be applied to cotyl cutters or other cutting guiding devices. In particular, the volume of the part of the layer 6 forming skin comprising the parts 5 of teeth intended to act on the bone is much smaller than the total volume of the rasp and also much smaller than the volume of the interior part that it surrounds. Thus, the ratio between the volume defined by the exterior surface of the layer 6 forming the teeth 5 is at least ten times greater than the volume of the layer 6 itself. Preferably, it is at least one hundred times greater. Between the layer 6 and the central part 3 an interface is formed between the plastic materials. This interface is present whether the two materials are identical or not.

The width 1 of the tooth or each tooth 5, that is the smallest width dimension at the level of said one surface of the instrument from which it projects is less than 8 mm, preferably between 1 and 7 mm, in particular between 2 and 5 mm, more preferably between 3 and 4, for example 3.5 mm.

The height (h) of the tooth or each tooth, that is the distance between its tip and said one surface is greater than 0.5 mm, in particular is between 1 and 8 mm, for example is 1 mm.

The ratio of the width to the height is lower than 0.2, in particular between 0.15 and 2.0, for example 1/3.5 or 0.285.

Furthermore, the thickness of the layer 6 of plastic material is, apart from the teeth, preferably between 0.8 mm and 5 mm. In particular, the ratio of this thickness of the layer apart from the teeth to the height of the teeth is less than 10, preferably less than 5, in particular between 5 and 0.5.

It is also possible to form a cotyl cutter by following the same principle as the rasp of FIGS. 1 to 4. It thus has a central part comprising in particular in its core a metal rod and a skin forming the teeth for acting on the bone.

Furthermore, according to another embodiment it is possible to provide in the mould a system which closes the openings of the mould cavities and only opens them under the effect of pressure from the plastic moulding material, when only the volumes of the moulding cavities for teeth remain unfilled. This results in a method such that the moulding material penetrates well into said cavities. It is thus possible to produce teeth with the desired thin profile.

By means of this process the moulding can be performed in a single step and not only are perfectly formed teeth obtained but also, if necessary, no interface is formed in the plastic material or between the plastic materials.

It is also possible, within the scope of the present invention, to make sure that the preform, in particular made of metal, stands out from the skin in some parts, for example to form teeth.

What is claimed is:

1. A method for producing by moulding a surgical instrument for an action on a bone for removing part of said bone, one part of said instrument being designed to withstand an increased stress associated with said action and to be in contact with said bone during said action and being made of plastic material only, comprising the steps of:
   preparing a mould corresponding to a final shape of the instrument,
   beforehand forming a first part of the instrument, said first part not comprising said one part and the forming of said first part being so that said first part is in said mould and leaves unfilled only a closed space relating to said one part, and
   forming said one part by moulding by opening said space then filling said space to obtain the surgical instrument in this way by moulding.

2. The method according to claim 1, wherein said one part comprises at least one tooth projecting from said instrument and intended to act on the bone directly.

3. The method according to claim 1, wherein the first part is an interior part and said one part surrounds the first part.

4. The method according to claim 3, wherein the interior part is a preform.

5. The method according to claim 4, wherein the preform is in the form of a metal rod inserted into the mould prior to the moulding of said one part.

6. The method according to claim 1, wherein the volume of the first part is greater than the volume of said one part.

7. The method according to claim 2, wherein the smallest width dimension of the tooth or each tooth at said instrument from which it projects is between 1 mm and 7 mm.

8. The method according to claim 7, wherein a height of the tooth or each tooth, wherein the height is the distance between a tip and a surface of the tooth or each tooth, is greater than or equal to 1 mm.

9. The method according to claim 8, wherein a ration of the height to the width is greater than 0.2.

10. The method according to claim 1, wherein said instrument is a femoral rasp.

\* \* \* \* \*